(12) United States Patent
Latiolais

(10) Patent No.: US 10,933,194 B2
(45) Date of Patent: Mar. 2, 2021

(54) SYRINGE FOR AND METHOD OF DELIVERING A VOLUME OF SOLUTION

(71) Applicant: Lon J. Latiolais, Georgetown, TX (US)

(72) Inventor: Lon J. Latiolais, Georgetown, TX (US)

(73) Assignee: VYLON IP HOLDING, LLC, Breaux Bridge, LA (US)

( * ) Notice: Subject to any disclaimer, the term of this patent is extended or adjusted under 35 U.S.C. 154(b) by 337 days.

(21) Appl. No.: 14/563,702

(22) Filed: Dec. 8, 2014

(65) Prior Publication Data

US 2016/0158101 A1 Jun. 9, 2016

(51) Int. Cl.
*A61M 5/28* (2006.01)
*A61M 5/24* (2006.01)

(52) U.S. Cl.
CPC ............... *A61M 5/28* (2013.01); *A61M 5/24* (2013.01); *A61M 2005/2407* (2013.01); *A61M 2005/2485* (2013.01)

(58) Field of Classification Search
CPC .. A61M 2005/2414; A61M 2005/2437; A61M 5/24; A61M 5/3129
USPC ....................................................... 604/506
See application file for complete search history.

(56) References Cited

U.S. PATENT DOCUMENTS

| | | | |
|---|---|---|---|
| 3,767,085 A * | 10/1973 | Cannon | B01F 13/002 222/82 |
| 3,848,593 A | 11/1974 | Baldwin | |
| 4,919,657 A | 4/1990 | Haber et al. | |
| 5,137,528 A | 8/1992 | Crose | |
| 5,542,934 A | 8/1996 | Silver | |
| 5,603,695 A | 2/1997 | Erickson | |
| 6,312,413 B1 | 11/2001 | Jensen et al. | |
| 2002/0055720 A1 | 5/2002 | Hohlfelder et al. | |
| 2005/0101913 A1 | 5/2005 | Hohlfelder et al. | |
| 2007/0060875 A1 | 3/2007 | Bassarab et al. | |
| 2009/0182301 A1 | 7/2009 | Bassarab et al. | |
| 2012/0214124 A1 * | 8/2012 | McLelland | A61J 1/062 433/90 |

FOREIGN PATENT DOCUMENTS

| | | |
|---|---|---|
| EP | 2407194 A1 | 1/2012 |
| WO | 1997025932 A1 | 7/1997 |

OTHER PUBLICATIONS

Dental Products Report, Dec. 17, 2012, introduction of VibraJect from ITL Dental.

* cited by examiner

*Primary Examiner* — Phillip A Gray
(74) *Attorney, Agent, or Firm* — Matthews, Lawson, McCutcheon & Joseph, PLLC

(57) ABSTRACT

Methods and apparatuses are disclosed with regard to syringe-transfer of a solution or other fluid within a carpule. One embodiment includes an apparatus that is a non-standard carpule barrel having a top portion, a bottom portion, and a barrel portion therebetween. The top portion includes an opening for receiving a syringe plunger and at least a first portion of a connection mechanism for connecting to an upper portion of the syringe. The bottom portion includes another opening capable of holding a bottom end of the carpule, wherein the carpule may be a standard carpule or a non-standard carpule. The barrel portion is located between the top portion and bottom portion, wherein the barrel portion includes a cradle, and wherein the cradle has a length capable of holding a standard carpule or a non-standard carpule and a width greater than the standard carpule.

24 Claims, 3 Drawing Sheets

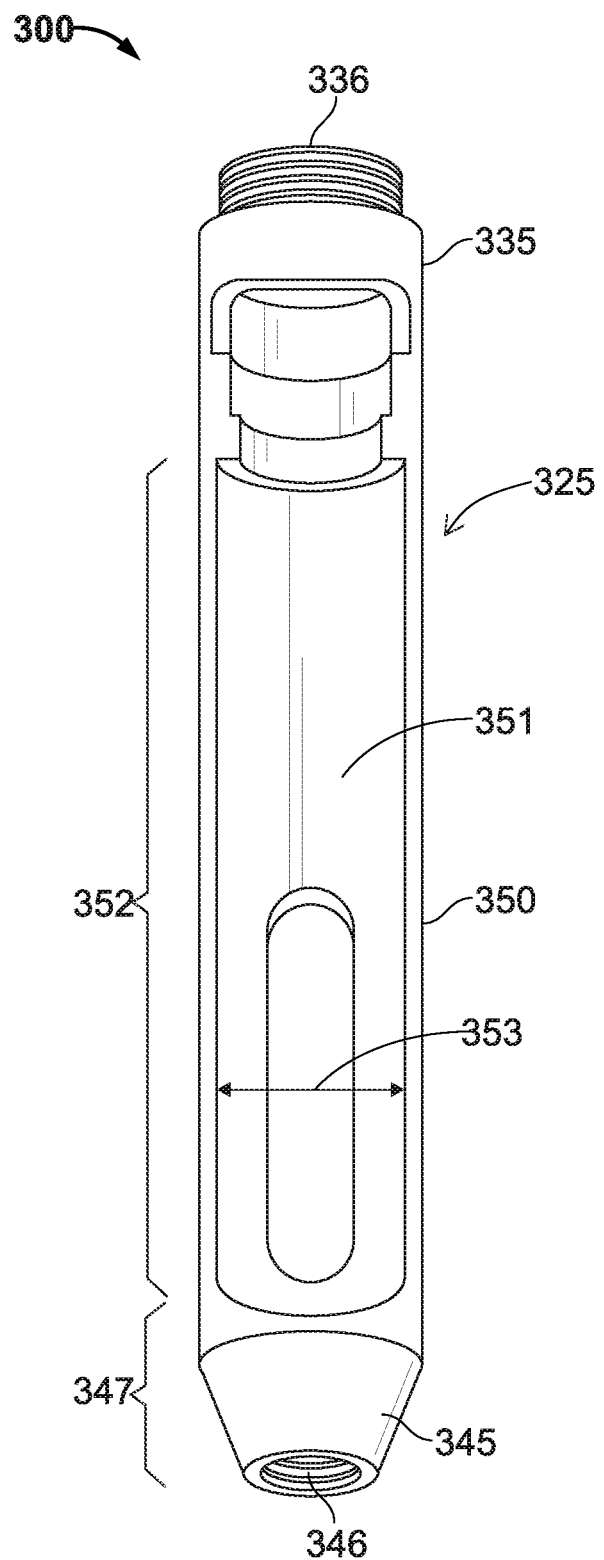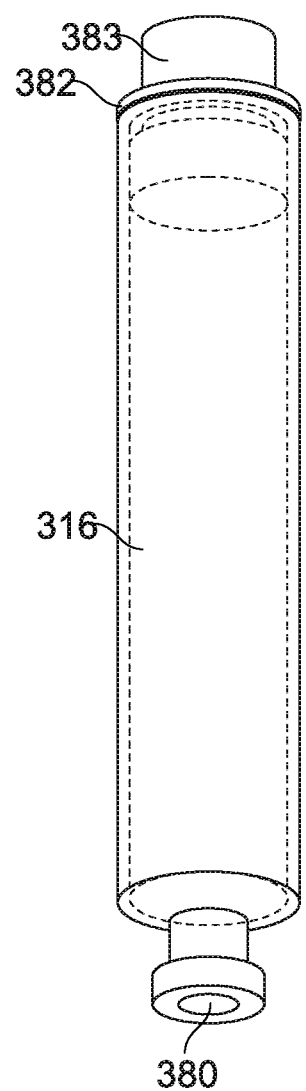
FIG. 3A
FIG. 3B

SYRINGE FOR AND METHOD OF DELIVERING A VOLUME OF SOLUTION

FIELD OF DISCLOSURE

The disclosure relates, generally, to methods and apparatuses that permit delivery of a different volume, whether more or less, of a fluid, e.g., medicine, as compared to the volume delivered through the use of a standard carpule in a syringe.

BACKGROUND

In the medical field, a syringe is an apparatus or device that is a commonplace tool for injecting and delivering a fluid into a patient or withdrawing a fluid or material from a patient, e.g., human or non-human, for medical and/or preventative reasons. When delivering the fluid (e.g., a medicine comprising an anesthetic, an analgesic, or other fluid injected, infused and/or delivered for medical and/or preventative reasons), the syringe may be loaded with a standard carpule, which may contain the medicine or other fluid that reaches the patient by someone pushing downwardly on the syringe's plunger rod that terminates in a hook, which pierces the top of the standard carpule. After this piercing, the medicine or other fluid is pushed out of the syringe's needle by someone continuing to push downwardly on the syringe's plunger rod, so that the movable plug within the standard carpule moves down the standard carpule. Once the movable plug is at the bottom of the standard carpule, another standard carpule must be loaded into the syringe in order to provide the patient with additional medicine or other fluids. The changing and/or re-loading of multiple carpules into the syringe, in addition to the necessity for multiple injections for delivery of the medicine contained within the multiple carpules, creates health risks for physicians and patients, in addition to increasing the costs associated with materials, time, labor and other resources.

Apparatuses and methods for delivery or withdrawal of a volume of fluid greater than a standard carpule volume are desired and needed to reduce: (1) health risks associated with multiple injections (needle-sticks) and the use of multiple carpules; (2) costs associated with the manufacturing of multiple carpules; (3) costs associated with the use of the materials required for the manufacturing of multiple carpules; (4) excess time required in delivering or withdrawing multiple carpules because a volume of solution, greater than the volume held by a standard carpule, is needed; and (5) the emotional trauma experienced by patients having to receive multiple injections due to the need for multiple carpules.

SUMMARY

One example embodiment includes a method for transferring a fluid that comprises applying a force with a syringe plunger, wherein the applied force causes the syringe plunger to forcibly connect to a non-standard carpule loaded into a barrel of a syringe, wherein the non-standard carpule has a volume that is different from a standard carpule. The method may continue by including the steps of moving a solution or other fluid through a syringe needle, which may be in fluid communication with the non-standard carpule, and adjusting the volume of the solution or other fluid in the non-standard carpule, subsequent to step of the injecting or applying the force to the syringe plunger. In an embodiment, the barrel of the syringe may be removable from the syringe and interchangeable, such that the barrel may be a standard barrel or a non-standard barrel having a capability of holding different volumes of fluid.

In another example embodiment, the applied force to the syringe plunger may include pushing down on the syringe plunger to connect to a non-standard carpule, inserting the syringe plunger into the non-standard carpule, or combinations thereof. In an alternative, example embodiment, the applied force to the syringe plunger may include pulling upwards on the syringe plunger to at least partially fill the non-standard carpule with a fluid.

In yet another example embodiment, there is a method for delivering a solution or other fluid, wherein the method includes loading a non-standard carpule into a syringe having a non-standard carpule barrel, and wherein the non-standard carpule may have a volume that is different (e.g., greater or smaller) from a standard carpule. The syringe may further include a syringe plunger and syringe needle, and the steps of the method may include applying a force to the syringe plunger for pushing a volume of the solution or other fluid within the non-standard carpule towards the syringe needle. The steps of the method may further include emitting at least a portion of the volume of the solution, or other fluid, from the syringe needle that is in fluid communication with the non-standard carpule.

The syringe may include an upper portion and a bottom portion, and the upper portion of the syringe may be connected to a top portion of the non-standard carpule barrel, which may be removable or irremovable from the syringe. In an embodiment, the connecting of the top portion of the non-standard carpule barrel to the upper portion of the syringe may be removable, and the removable connection may include the use of threading, screwing, latching, snapping, or combinations thereof, for the removable connection. In an alternative, example embodiment, the connecting of the top portion of the non-standard carpule barrel to the upper portion of the syringe may be irremovable, and the irremovable connection may include the use of welding, bonding, fusing, or combinations thereof. In an embodiment, an interchangeable barrel may be connected to the upper portion of the syringe, prior to connecting the top portion of the removable non-standard carpule barrel to the upper portion of the syringe.

In still another example embodiment, the syringe needle may be connected to a bottom portion of the non-standard carpule barrel, which is removable or irremovable from the syringe. The connecting of the syringe needle may be removably or irremovably connected to the bottom portion of the non-standard carpule barrel. In an embodiment, the syringe needle may be removably connected to a bottom portion of a removable non-standard carpule barrel, and the removable connection may include threading, screwing, latching, snapping, or combinations thereof. In an alternative embodiment, the syringe needle may be irremovably connected to a bottom portion of a removable non-standard carpule barrel, and the irremovable connection may include welding, bonding, fusing, or combinations thereof.

In an embodiment, a removable non-standard carpule barrel, a non-standard carpule, at least a portion of a syringe, or combinations thereof, may be autoclavable for re-use. In an alternative embodiment, a removable non-standard carpule barrel, a non-standard carpule, at least a portion of a syringe, or combinations thereof, may be disposable after a first or single use.

In an embodiment of the methods for delivering a fluid, the emitting may include emitting, from a non-standard carpule, a greater volume of fluid than the volume of fluid held within a standard carpule.

In another embodiment, an apparatus is usable for injection and/or delivery of a fluid, and the apparatus may include a removable non-standard carpule barrel having a top portion, a bottom portion, and a barrel portion therebetween. The top portion may include an opening for receiving a syringe plunger and at least a first portion of a connection mechanism for connecting to an upper portion of the syringe. The bottom portion may include another opening capable of holding a bottom end of a carpule, which may include a standard carpule or a non-standard carpule, both of which may be removable from the syringe. The top portion may be integrally or removably connected to an upper portion of the syringe, and/or the bottom portion may be integrally or removably connected to a syringe needle portion, optionally including the needle of the syringe.

The non-standard barrel portion may be located between the top portion and bottom portion, and the barrel portion may include a cradle. In an embodiment, the cradle may have a length that may be capable of holding a removable standard carpule or a removable non-standard carpule, and the cradle may have a width that may be greater than a standard carpule, which may be removable.

In an embodiment, a removable non-standard carpule barrel may be located in a lower portion of a syringe. In an embodiment, the bottom portion of the syringe may have a convex portion above the another opening, for connecting to a syringe needle portion and/or syringe needle.

In an embodiment, a removable non-standard carpule barrel may include a cradle that may have a width that may be sufficient to hold a volume within a non-standard carpule that is at least twice as large as the volume of a standard carpule. In another embodiment, the cradle may hold a removable non-standard carpule that may have a maximum volume capacity that is smaller than the maximum volume capacity of a standard carpule.

In an embodiment, the top portion of the non-standard carpule barrel may form a removable or irremovable connection with the upper portion of the syringe, and the bottom portion forms a removable or irremovable connection with a syringe needle portion of the syringe.

In an embodiment, at least part of the removable non-standard carpule barrel, the upper portion of the syringe, the lower portion of the syringe, or combinations thereof may be autoclavable for re-use. In an alternative embodiment, at least part of the removable non-standard carpule barrel, the upper portion of the syringe, the lower portion of the syringe, or combinations thereof is disposable after a single or first use.

In an embodiment, the non-standard carpule barrel may be removable or irremovable and may be loaded with removable non-standard carpule that may include an integrated or removable plug for insertion into a cavity located at a top end of the removable non-standard carpule.

BRIEF DESCRIPTION OF THE DRAWINGS

So that the manner in which the above recited features, advantages and objects of this disclosure are attained and may be understood in detail, a more particular description, briefly summarized above, may be had by reference to the embodiments thereof which are illustrated in the appended drawings.

It is to be noted, however, that the appended drawings illustrate only typical embodiments of this disclosure and are therefore not to be considered limiting of its scope, for the disclosure may admit to other equally effective embodiments.

FIG. 3B depicts an example embodiment of a non-standard carpule having a plug in its cavity alongside FIG. 3A, which depicts a non-standard carpule barrel in accordance with the disclosed methods and apparatuses.

DESCRIPTION OF EXAMPLE EMBODIMENTS

The following is a detailed description of example embodiments accompanied by drawings. The embodiments are examples and are in such detail as to clearly communicate the claimed invention. However, the amount of detail offered is not intended to limit the anticipated variations of embodiments; on the contrary, the intention is to cover all modifications, equivalents, and alternatives falling within the spirit and scope of the invention as defined by the claims. The detailed descriptions below are designed to make such embodiments obvious to a person of ordinary skill in the art.

In addition, directional terms, such as "above," "below," "upper," "lower," "front," "back," "top," "bottom," etc., are used for convenience in referring to the accompanying drawings. In general, "above," "upper," "upward," "top," and similar terms refer to a direction away the earth's surface, and "below," "lower," "downward," "bottom," and similar terms refer to a direction toward the earth's surface, but is meant for illustrative purposes only, and the terms are not meant to limit the disclosure.

Generally disclosed are methods and apparatuses for transfer of a solution or other fluid to or from a body (e.g., human or non-human patient) by use of a syringe having a carpule, i.e., non-standard carpule, which has a different size, whether smaller or larger, than a standard carpule, which generally holds a 1.8 mL volume of fluid. Henceforth, the transfer of the solution or other fluid discussion continues in terms of delivering a medicine within a non-standard carpule, but, it is understood that the discussion equally applies to withdrawing solution(s) or other fluid(s) from a body, e.g., a human or non-human patient, into the non-standard carpule.

Figure 1:
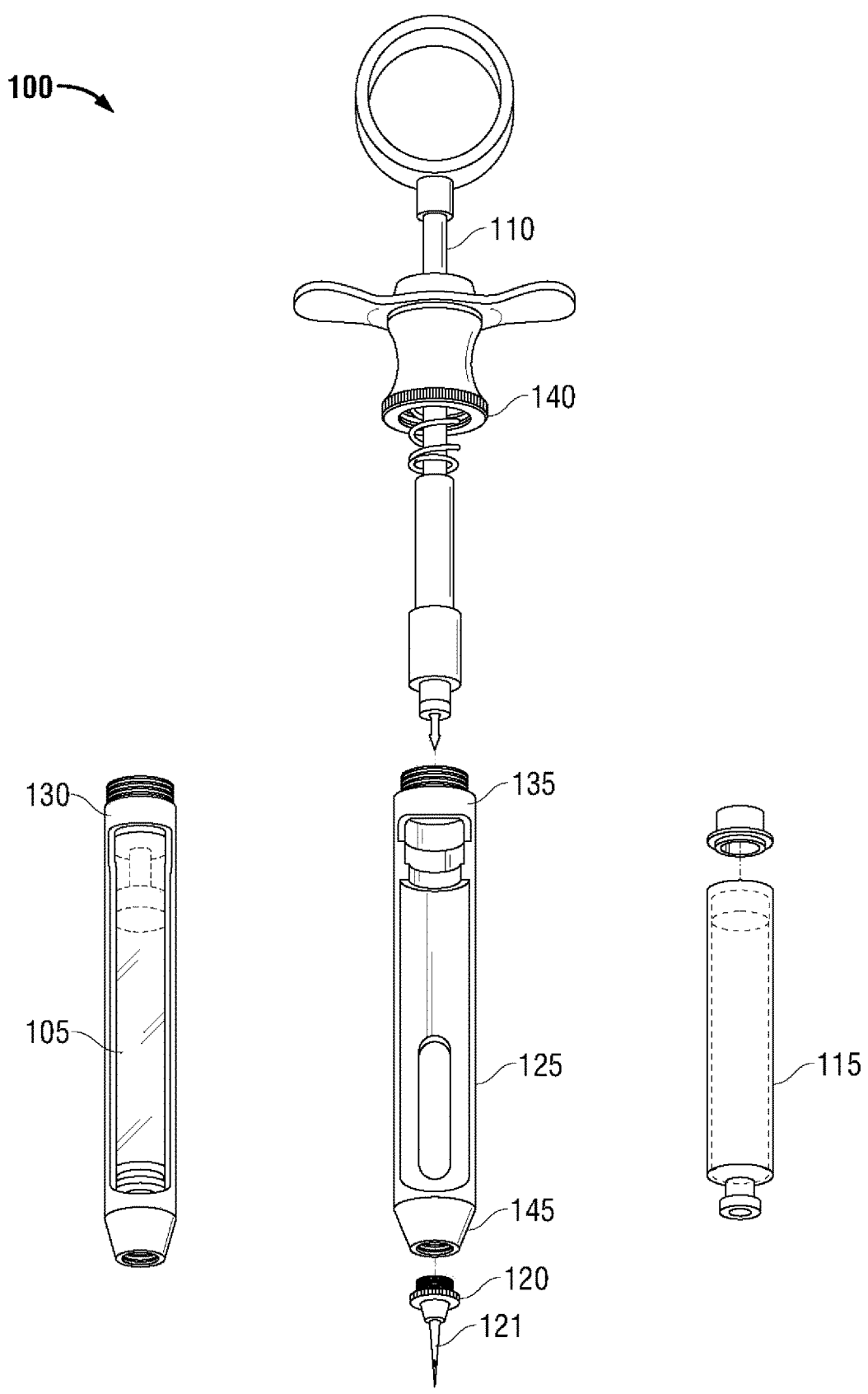
FIG. 1 depicts an exploded view of a syringe, wherein shown are example embodiments of syringe components that include an upper portion having a syringe plunger, a non-standard carpule barrel, a syringe needle portion having a needle, a non-standard carpule, a plug, and a standard carpule loaded in a barrel in accordance with the disclosed methods and apparatuses.

With reference to FIG. 1, disclosed are methods and apparatuses for transferring a fluid, wherein the fluid may be an injectable medicine, solution or other fluid. The method may include applying a force to a syringe plunger 110, to act upon a non-standard carpule 115 loaded into a syringe 100, wherein the non-standard carpule 115 has a volume that is different (i.e., greater or less than) from the volume of fluid contained within a standard carpule 105. If the object, for example, is to decrease the number of shots of medicine to inject into a patient, then the non-standard carpule 115 in the syringe 100 is likely larger than the standard carpule 105, due to the capability of the non-standard carpule 115 to hold a greater volume of medicine. Subsequent to applying the force, the solution in the non-standard carpule 115 may move through the syringe needle 121, located at the bottom of the syringe 100, wherein the syringe needle 121 may be in fluid communication with the non-standard carpule 115 having the fluid, e.g., medicine, solutions, or other fluids. The volume of the fluid in the non-standard carpule 115 may adjust subsequent to the applying of the force and the moving of the solution through the syringe needle 121. In the instance where applying the force involves pushing down on the syringe plunger 110, then the volume of the solution within the non-standard carpule 115 may adjust so as to increase in the volume of the fluid. In the opposite instance where applying the force involves pulling up on the syringe plunger 110, then the volume of the fluid within the non-standard carpule 110 may adjust so as to decrease in the volume of the fluid.

Figure 2:
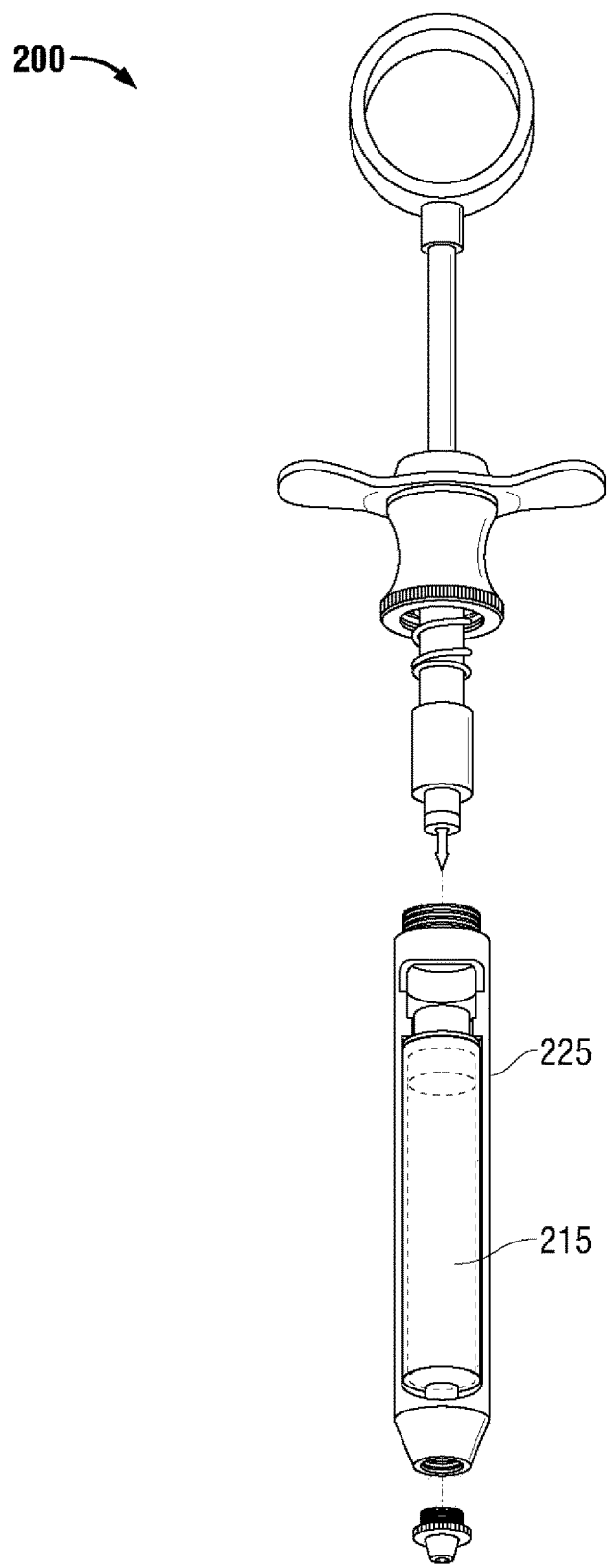
FIG. 2 depicts an example embodiment of a syringe having an upper portion with a syringe plunger separated from a lower portion, which includes a non-standard carpule loaded in a non-standard carpule barrel that is separated from a syringe needle portion in accordance with the disclosed methods and apparatuses.

Embodiments include apparatuses and methods usable for delivering a solution or other fluid from a syringe 100 to a body (e.g., human patient or non-human patient). With reference to FIGS. 1 and 2, the steps of the methods may include loading a non-standard carpule 115, 215 into a syringe 100, 200 having a non-standard carpule barrel 125, 225, which may differ in dimensions regarding length, width, size, shape, and/or circumference, as compared to a standard carpule barrel 130. Loading the non-standard carpule or loading the syringe may be understood to mean placing the non-standard carpule 115, 215 within the non-standard carpule barrel 125, 225. As previously discussed and with reference to FIG. 1, the non-standard carpule 115 has a volume that is different from a standard carpule 105. Within the volume of the non-standard carpule may be a fluid, which may comprise a solution of medicine or another substance.

Subsequent to loading the syringe 100 with the non-standard carpule, the steps of the methods may include exerting a force on the syringe plunger 110 and pushing down, using the force applied to the syringe plunger 110, on the fluid within the non-standard carpule 115, which may result in emitting the fluid from a needle 121 of the syringe 100, which is in fluid communication with the non-standard carpule 115. When the volume of the fluid within the non-standard carpule 115 is greater than the volume capable of being held by a standard carpule 105, then it follows that the emitting step may result in emitting a greater volume of solution than that which is capable of being held and emitted by a standard carpule 105. The non-standard carpule 115 may or may not be designed to be disposable after a single use. Considerations of disposability may include cost and biodegradability of the material (e.g., inert plastics such as polycarbonates or any type of material) used for constructing the non-standard carpule 115, wherein autoclaving or other sterilizing methods may permit an effective re-use of the non-standard carpule, as well as the syringe, including the non-standard carpule barrel of the syringe.

In returning to FIG. 1, the apparatus and methods may include connecting a top portion 135 of the non-standard carpule barrel 125 to an upper portion 140 of the syringe 100. In alternative example embodiments, the non-standard carpule barrel 125 may be removably connected or non-removably connected to an upper portion 140 of the syringe 100. In the removable case, the connection may be consummated by any known means, such as screwing/unsrewing, snapping/unsnapping, latching/unlatching, or other forms of removable mating or connecting. In the non-removable case, the irremovable connection may be consummated by any known means, such as by injection molding, wherein the upper portion 140 and the non-standard carpule barrel 125 are part of a unified piece of plastic or other moldable material. Other forms, usable for forming a non-removable connection between the top portion 135 of the non-standard carpule barrel 125 and the upper portion 140 of the syringe 100, may include welding, bonding, or fusing the two portions together, as well as other forms of irremovable mating.

Returning to the removable case, the syringe 100 may permit modularity or inter-changeability through use of a removable barrel. That is, prior to removably connecting the non-standard carpule barrel 125 to the upper portion 140 of the syringe 100, it may be necessary to remove a barrel already connected to the upper portion 140 of the syringe 100. Such inter-changeability or modularity may comprise exchanging one non-standard carpule barrel for another non-standard carpule barrel or for a standard carpule barrel.

Similarly, the disclosed methods and apparatuses may include connecting the needle 121 of the syringe 100, such as through a syringe needle portion 120, to a bottom portion 145 of the non-standard carpule barrel 125. In the removable case, the connection may be consummated by any known means, such as screwing/unscrewing, snapping/unsnapping, latching/unlatching, or other forms of removable mating and/or connecting. In the non-removable case, the irremovable or permanent connection may be consummated by any known means, such as by injection molding, wherein the bottom portion 145 and the non-standard carpule barrel 125 are part of a unified piece of plastic or other moldable material. Other forms, usable for forming a non-removable connection between the bottom portion 140 of the non-standard carpule barrel 125 and the syringe needle portion 120, may include welding, bonding, or fusing the two portions together, as well as other forms of irremovable mating.

In view of the removable and irremovable components of the syringe 100 disclosed herein, the disclosed apparatus and methods may permit all or part of the syringe 100, such as the non-standard carpule barrel 125, the non-standard carpule 115, or combinations thereof, and so forth to be made of materials capable of being autoclaved.

With reference to FIG. 3A, further discussion of the non-standard carpule barrel 325 now ensues. The non-standard carpule barrel 325, may be interchangeable (removable) and may constitute the lower portion 300 of the syringe (100 in FIG. 1), alongside an optional connection to a syringe needle (121 in FIG. 1). The non-standard carpule barrel 325 may include a top portion 335, a bottom portion 345, and a barrel portion 350 therebetween. As shown, the top portion 335 may include an opening 336 for receiving a syringe plunger (110 in FIG. 1), and at least a first portion of a connection mechanism for connecting to an upper portion (140 in FIG. 1) of the syringe (100 in FIG. 1). In an embodiment, the first portion of the connection mechanism may include threading, a latch, a snap, a weld, or other removable components or mechanisms for consummating a removable connection with the upper portion (140 in FIG. 1) of the syringe 100, as previously discussed. As such, the upper portion (140 in FIG. 1) of the syringe (100 in FIG. 1) may connect to a complimentary and removably connectable second portion (i.e., the first portion of the connection mechanism) for consummating a removable connection between the upper portion (140 in FIG. 1) of the syringe and the top portion 335 of the non-standard carpule barrel 325. In an alternative embodiment, the first portion of the connection mechanism of the top portion 335 may form a non-removable or permanent connection with the upper portion (140 in FIG. 1) of the syringe (100 in FIG. 1), such that the upper portion (140 in FIG. 1) of the syringe (100 in FIG. 1) connects to the top of the non-standard carpule barrel 325, and there are no separate sections of the non-standard carpule barrel 325, such that the joined upper portion (140 in FIG. 1) and lower portion 300 of the syringe form a continuous syringe structure.

As shown in FIG. 3A, the bottom portion 345 of the non-standard carpule barrel 325 includes another opening 346 that may be capable of holding a bottom end 380 of a carpule, which may be a standard carpule (105 in FIG. 1) or a non-standard carpule 316. The barrel portion 350 of the non-standard carpule barrel 325 is shown in FIG. 3B and is located between the top portion 335 and the bottom portion 345, wherein the barrel portion 350 may comprise a cradle 351 for holding the carpule. The cradle 351 may have a length 352 for holding a standard or non-standard carpule and a width 353 that may hold the standard carpule, or a width for holding a non-standard carpule that is greater than the width required for holding the standard carpule (105 in FIG. 1). A point to be made here is that, for example, the non-standard carpule barrel 325 may hold a non-standard carpule 316 that has the same length as a standard carpule (105 in FIG. 1), but a different width as compared to a standard carpule (105 in FIG. 1), wherein the different width, for example, may be wider so that a greater volume of fluid may be delivered through a single use of a carpule-loaded syringe.

Similar to the foregoing discussion of the top portion 335 having a connection mechanism for connecting to an upper portion (140 in FIG. 1) of the syringe (100 in FIG. 1), the same connectability discussion may be applied to the bottom portion 345. That is, in an embodiment, the bottom portion 345 may comprise a connection mechanism at its opening 346, which may be threaded, latched, snapped, welded, or removably connected by any other means, for connecting to the syringe needle portion (120 of FIG. 1). In an alternative embodiment, the connection mechanism may be irremovably or permanently connected with syringe needle portion (120 in FIG. 1), forming one continuous syringe structure. Further, the syringe needle (121 in FIG. 1) may be removably or irremovably connected with the syringe needle portion (120 in FIG. 1).

The bottom portion 345 of the non-standard carpule barrel 325 may include a convex portion 347 located above the another opening 346. The convexity may aid in holding the loaded carpule within the non-standard carpule barrel 325. As discussed above, the width 353 of the cradle 351 may be wide enough to hold a non-standard carpule, having the added limitation in this case that the non-standard carpule is larger (e.g., wider) than the standard carpule. For example, in such an instance, the non-standard carpule may be at least twice as large as a standard carpule. In another example embodiment, the cradle 351 may hold a non-standard carpule having a maximum volume capacity that is smaller than the maximum volume capacity of a standard carpule. The non-standard carpule, itself, may have a tapered bottom end 380 and a top end 382, wherein the top end 382 has a cavity that includes an optionally integrated or removable plug 383, such as one made from rubber, plastic, or other material. The plug 383 may assist in holding the loaded carpule within the non-standard carpule barrel 325.

While the foregoing is directed to example embodiments, other and further embodiments may be devised without departing from the basic scope thereof, and the scope thereof is determined by the claims that follow.

What is claimed is:

1. A method of transferring a fluid, the method comprising:
    applying a force to a syringe plunger, wherein the force causes the syringe plunger to forcibly connect to a standard carpule or non-standard carpule loaded into an interchangeable barrel of a syringe, wherein the interchangeable barrel includes a single longitudinal central axis extending from a top portion of the interchangeable barrel to a bottom portion of the interchangeable barrel and through a longitudinal radial center of the interchangeable barrel, wherein the interchangeable barrel includes an outer diameter, and is configured to hold standard and non-standard size carpules completely within the outer diameter so that the single longitudinal central axis extends through a volume of the standard and non-standard carpules, the volume being a space for containing fluid, and wherein the volume of the non-standard carpule is different from the volume of the standard carpule;
    moving, subsequent to the applying, the fluid through a syringe needle in fluid communication with the non-standard carpule; and
    adjusting, subsequent to the moving, an amount of the fluid in the non-standard carpule using the force.

2. The method of claim 1, wherein the applying comprises pushing down on the syringe plunger for connecting to the standard carpule or non-standard carpule, pushing down on the syringe plunger for inserting into the standard carpule or non-standard carpule, and combinations thereof.

3. The method of claim 1, further comprising applying the force in relation to the syringe plunger, wherein the force comprises pulling up on the syringe plunger in order to at least partially fill the standard carpule or non-standard carpule with the fluid.

4. A method for delivering a fluid, the method comprising:
    loading a standard carpule or non-standard carpule into a removable, carpule barrel of a syringe, wherein the carpule barrel includes a single longitudinal central axis extending from a top portion of the carpule barrel to a bottom portion of the carpule barrel and through a longitudinal radial center of the carpule barrel, wherein the carpule barrel includes an outer diameter, and is configured to hold standard and non-standard size carpules completely within the outer diameter so that the single longitudinal central axis extends through a volume of the standard and non-standard carpules, the volume being a space for containing fluid, wherein the syringe further comprises a syringe plunger and a syringe needle, and wherein the volume of the non-standard carpule is different from the volume of the standard carpule;
    applying a force to the syringe plunger for pushing the fluid within the standard carpule or non-standard carpule towards the syringe needle; and
    emitting at least a portion of the fluid from the syringe needle in fluid communication with the standard carpule or non-standard carpule.

5. The method of claim 4, further comprising the syringe having an upper portion and a bottom portion, and connecting a top portion of the removable carpule barrel to the upper portion of the syringe.

6. The method of claim 5, wherein the connecting comprises an irremovable connection between the top portion of the removable carpule barrel and the upper portion of the syringe, and wherein the irremovable connection comprises welding, bonding, fusing, and combinations thereof.

7. The method of claim 5, wherein the connecting comprises a removable connection between the top portion of the carpule barrel and the upper portion of the syringe, and wherein the removable connection comprises threading, screwing, latching, snapping, and combinations thereof.

8. The method of claim 4, further comprising removing, prior to connecting the top portion of the removable carpule barrel to the upper portion of the syringe, an interchangeable barrel connected to the upper portion of the syringe.

9. The method of claim 4, further comprising connecting the syringe needle to a bottom portion of the removable carpule barrel.

10. The method of claim 9, wherein the connecting comprises removably connecting the syringe needle to the bottom portion of the removable carpule barrel, and wherein the removable connection comprises threading, screwing, latching, snapping, and combinations thereof.

11. The method of claim 9, wherein the connecting comprises irremovably connecting the syringe needle to the bottom portion of the removable carpule barrel, and wherein the irremovable connection comprises welding, bonding, fusing, and combinations thereof.

12. The method of claim 4, further comprising autoclaving the removable carpule barrel, the standard carpule or non-standard carpule, at least a portion of the syringe, and combinations thereof, for re-use.

13. The method of claim 4, further comprising disposing of the removable carpule barrel, the standard carpule or non-standard carpule, at least a portion of the syringe, and combinations thereof, after a single use.

14. A removable non-standard carpule barrel comprising:
a top portion comprising an opening for receiving a syringe plunger and at least a first portion of a connection mechanism for connecting to an upper portion of a syringe;
a bottom portion comprising another opening configured to hold standard and non-standard carpules; and
a barrel portion located between the top portion and the bottom portion, wherein the barrel portion comprises a single longitudinal central axis extending from the top portion to the bottom portion and through a longitudinal radial center of the barrel portion, and comprises a cradle including an outer diameter, wherein the cradle has a size configured for holding standard and non-standard carpules completely within the outer diameter so that the single longitudinal central axis extends through a volume of the standard and non-standard carpules, the volume being a space for containing fluid.

15. The removable non-standard carpule barrel of claim 14, wherein the removable non-standard carpule barrel is located in a lower portion of the syringe.

16. The removable non-standard carpule barrel of claim 14, wherein the bottom portion has a convex portion above the bottom portion opening.

17. The removable non-standard carpule barrel of claim 14, wherein the top portion forms a removable connection with the upper portion of the syringe.

18. The removable non-standard carpule barrel of claim 14, wherein the bottom portion forms a removable connection with a syringe needle portion of the syringe.

19. The removable non-standard carpule barrel of claim 14, further comprising a syringe needle connected to or held within a syringe needle portion connected to the bottom portion.

20. The removable non-standard carpule barrel of claim 14, wherein at least part of the removable non-standard carpule barrel, the upper portion of the syringe, the lower portion of the syringe, and combinations thereof is autoclavable.

21. The removable non-standard carpule barrel of claim 14, wherein at least part of the removable non-standard carpule barrel, the upper portion of the syringe, the lower portion of the syringe, and combinations thereof is disposable.

22. The removable non-standard carpule barrel of claim 14, further comprising a removable carpule loaded within the removable non-standard carpule barrel of the syringe.

23. The removable non-standard carpule barrel of claim 14, further comprising a plug for insertion into a cavity located at a top end of the removable non-standard carpule.

24. A method for delivering a fluid, the method comprising:
loading a standard carpule or non-standard carpule within a barrel portion of a carpule barrel of a syringe, wherein the carpule barrel includes a single longitudinal central axis extending from a top portion of the carpule barrel to a bottom portion of the carpule barrel and through a longitudinal radial center of the carpule barrel, wherein the carpule barrel comprises and an outer diameter, and is configured to hold standard and non-standard carpules completely within the outer diameter so that the single longitudinal central axis extends through a volume of the standard and non-standard carpules, the volume being a space for containing fluid, wherein the syringe further comprises a syringe plunger and a syringe needle, and wherein the volume of the non-standard carpule is different than the volume of the standard carpule;
applying a force to the syringe plunger for pushing the fluid within the standard carpule or non-standard carpule towards the syringe needle; and
emitting at least a portion of the fluid from the syringe needle in fluid communication with the standard carpule or non-standard carpule.

* * * * *